United States Patent [19]

Fizet

[11] Patent Number: 5,487,817
[45] Date of Patent: Jan. 30, 1996

[54] PROCESS FOR TOCOPHEROLS AND STEROLS FROM NATURAL SOURCES

[75] Inventor: Christian Fizet, Zimmersheim, France

[73] Assignee: Hoffmann-La Roche Inc., Nutley, N.J.

[21] Appl. No.: 185,571

[22] Filed: Jan. 21, 1994

[30] Foreign Application Priority Data

Feb. 11, 1993 [CH] Switzerland ................... 467/93

[51] Int. Cl.$^6$ ..................... B01D 3/34; C07D 311/72
[52] U.S. Cl. ................ 203/38; 203/73; 203/80; 203/DIG. 16; 549/413; 552/545; 554/174; 554/175
[58] Field of Search .................. 203/38, 40, 73, 203/80, 71, DIG. 16; 549/413; 552/545; 554/174, 175

[56] References Cited

U.S. PATENT DOCUMENTS

| | | | |
|---|---|---|---|
| 2,704,764 | 3/1955 | Mattikow et al. | 549/413 |
| 2,866,797 | 12/1958 | Berry et al. | 552/545 |
| 3,108,120 | 10/1963 | Brown et al. | 549/413 |
| 3,122,565 | 2/1964 | Kijima et al. | 549/413 |
| 3,153,054 | 10/1964 | Brown et al. | 552/545 |
| 3,153,055 | 10/1964 | Brown et al. | 549/413 |
| 3,335,154 | 8/1967 | Smith et al. | 549/413 |

FOREIGN PATENT DOCUMENTS 7722349  3/1977  Japan .

OTHER PUBLICATIONS

CA 75(14):91267e.
CA 110(3):22549c.
CA 102(a): 77526h.
CA 99(15) 120897p.
CA 90(3):21088h.
CA 102(a):77397s.
Gavin, Arnold M., "Deordorization and Finished Oil Handling", *J. Amer. Oil Chemists Soc.*, 58, pp. 175–184 (Mar. 1981).
Ullmann's Enzyklopädie der techn. Chemie 23, 643–649 and 685–692 (Verlag Chemie, Weinheim 1983).

*Primary Examiner*—Virginia Manoharan
*Attorney, Agent, or Firm*—George M. Gould; George W. Johnston; Alan P. Kass

[57] ABSTRACT

A novel process for the recovery of tocopherols and sterols from natural, especially vegetable, sources. This process is especially a process for the separation of tocopherols and sterols from deodorizer sludges by distillation of these deodorizer sludges, in that prior to the distillation the sterols present in the deodorizer sludge are esterified with the fatty acids which are also present, the resulting mixture is distilled to obtain residual fatty acids and subsequently to obtain tocopherols, whereby the sterol esters formed in the esterification remain in the residue of this distillation, and then the tocopherols are isolated from the distillate and the sterols, after cleavage of their esters, are isolated from the distillation residue.

11 Claims, No Drawings

PROCESS FOR TOCOPHEROLS AND STEROLS FROM NATURAL SOURCES

The present invention is concerned with a novel process for the recovery of tocopherols and sterols from natural, especially vegetable, sources.

It is known that vegetable oils, such as, for example, sunflower oil, soya oil, rape oil, cottonseed oil, palm oil, groundnut oil, wheatgerm oil and the like, and fats are valuable natural sources of certain tocopherols and sterols. In addition to the mentioned tocopherols and sterols, such oils and fats also contain, inter alia, free fatty acids, waxes and glycerides. The recovery of natural tocopherols from these sources is of great importance, and this is also increasingly true for the recovery of natural sterols.

Numerous processes for the recovery of tocopherols and sterols from vegetable oils and fats are already known. Suitable starting materials which can be directly used in these processes are especially the distillates which are obtained in connection with the production of edible oils and fats after the deodorization step and which are commonly known as "deodorizer sludges" or "deodorizer distillates". The deodorizer sludge from the deodorization of soya oil is mainly used for this purpose, although deodorizer sludges from other vegetable oils are or can be used analogously. In general, the known technology utilizes the relatively low solubility of crystalline sterols in solvents, such as lower aliphatic alcohols and ketones, compared with the solubility of tocopherols in such solvents. One process for the isolation of sterols from vegetable sources, especially oils, is described in U.S. Pat. No. 2,866,797. In this process the fatty components of the vegetable source are saponified, the aqueous solution of the saponification products is extracted, for example with dichloroethylene, water and a water-miscible solvent, for example methanol or ethanol, are added to the extract and the resulting mixture is cooled in order to separate the sterols. Several other U.S. Patents, for example U.S. Pat. Nos. 3,335,154, 3,122,565, 2,704,764 and 3,153,055, describe processes for the isolation of tocopherols and sterols from deodorizer sludges. In each of these processes an essential process step comprises treating the deodorizer sludge with a lower aliphatic alcohol, for example methanol, normally in the presence of an acid catalyst. In accordance with the first of the four above-mentioned U.S. Patents, the deodorizer sludge is however previously subjected to saponification, followed by acidification. The treatment with alcohol is in each case an esterification of the free fatty acids present, which can be carried out, inter alia, at elevated is temperature (64–150° C. according to U.S. Pat. No. 2,704,764). Other typical processes are described in Ullmanns Enzyklopädie der techn. Chemie 23, 643–649 and 685–692, Verlag Chemie, Weinheim 1983, and U.S. Pat. Nos. 3,108,120 and 3,153,054. It must in general be noted that, according to the state of the art, the addition of a lower alcohol is required in order to esterify the fatty acids present in the deodorizer sludge.

The known procedures described above are complicated and expensive. It has now been found that the fatty acids and sterols already present in the respective deodorizer sludge can together form esters without essentially affecting tocopherols which are also present. These tocopherols and the esters formed from the esterification of the sterols with the fatty acids (hereinafter referred to as "sterol esters") can then be separated from one another on the basis of their different distillability and can be treated separately in order to finally obtain the separated tocopherols and sterols. This is the basis of the present invention, which is concerned especially with a process for the separation of tocopherols and sterols from deodorizer sludges by distillation of these deodorizer sludges, which process comprises, prior to the distillation, esterifying the sterols present in the deodorizer sludge with the fatty acids which are also present, distilling the resulting mixture to obtain residual fatty acids and subsequently to obtain tocopherols, whereby the sterol esters formed in the esterification remain in the residue of this distillation, and then isolating the tocopherols from the distillate and isolating the sterols, after cleavage of their esters, from the distillation residue. The esterification is preferably carried out by heating the deodorizer sludge at a temperature range of from about 150° C. to about 250° C., such as, for example, from about 150° C. to about 220° C., for from about 1 to about 12 hours, with higher temperatures generally requiring a shorter heating period.

As indicated above, the residues (distillates) from the deodorization of the usual edible oils, such as for example sunflower oil distillates, soya oil distillates, palm oil distillates etc., and fats especially come into consideration as deodorizer sludges. However, oils and fats which have not yet been deodorized can themselves also be used for this purpose, as can the mentioned residues which have already been subjected to a further concentration step. The preparation of such deodorizer sludges and the apparatus for this purpose have been widely described in the technical literature, for example in the article "Deodorization and Finished Oil Handling" by Arnold M. Gavin, *J. Amer. Oil Chemists Soc.* 58, 175–184, March 1981.

These deodorizer sludges usually contain the tocopherols as well as free fatty acids, glycerides of those acids which are normally present in oils and fats, fatty acid salts, sterols, waxes, squalene and a remainder comprising to some extent nonidentifiable accompanying substances. The term "tocopherols" embraces in the scope of the present invention not only the $\alpha$-, $\beta$-, $\gamma$- and $\delta$-tocopherols, but also the corresponding tocopherol homologues, for example tocotrienols, tocodienols and tocoenols, which can be present in relatively small amounts. The quantitative content of these substances usually varies very widely according to the nature of the starting materials and the process by which they are obtained. In the previously mentioned deodorization residues (distillates) the tocopherol content usually lies between about 1 and about 15 wt.% and that of sterols between about 4 and about 20 wt.%. The total content of free fatty acids, glycerides and salts usually amounts to about 40 to about 85 wt.% and that of the to some extent non-identifiable residues from about 5 to about 20 wt.%. In not yet deodorized fats and oils and in the already further concentrated deodorization residues these values lie, as is known, correspondingly lower and, respectively, higher.

According to the process in accordance with the invention, which comprises essentially a simple heating of the deodorizer sludge, the sterols present in the deodorizer sludge are esterified with the fatty acids which are also present. Thereby, in the subsequent distillation, already in a very early stage of the overall process for the separation of tocopherols and sterols from natural, especially vegetable, sources, a large part of the otherwise troublesome sterols can be removed as esters. Nevertheless, in the heating of the deodorizer sludge a small loss of tocopherols cannot be avoided or at least is very difficult to avoid, since the tocopherols can also form esters with the fatty acids, although with much smaller reaction velocity than that of the sterols.

Not only the sterol esters formed, but also glycerides (di- and triglycerides) and higher boiling components present in the deodorizer sludge remain as the residue after the heating. Campesterol, stigmasterol and sitosterol are the main examples of sterols which are converted into the corresponding sterol esters upon heating with the fatty acids. The actual sterol types depend, of course, on the nature (origin, production etc.) of the respective deodorizer sludge which is used.

A number of other reaction conditions can influence the course and the result of the heating. Thus, during the heating, the various tocopherols present in the deodorizer sludge do not behave exactly the same, that is certain tocopherols tend somewhat more (and of course undesirably) to participate in the esterification than others, which leads to a correspondingly differential loss of tocopherols. For example, in the case of α-tocopherol (for example in deodorizer sludge produced from sunflower oil) the loss is extremely low, while the content of γ- and δ-tocopherols under otherwise equal esterification conditions can decrease severely, which plays a greater role in the esterification of deodorizer sludge produced from soya oil. In this case, on the contrary, the ester formation from the fatty acids and sterols present is not or hardly influenced. The loss of tocopherols can be substantially reduced by previously de-gassing the deodorizer sludge, for example by about a half. In general, in all instances such a previous de-gassing is a preferred feature of the process in accordance with the invention. A typical de-gassing is effected at 60–70° C. at a pressure of about 20 mbar and for a duration of 15–20 minutes. Furthermore, the process can be effected at normal or elevated pressure, with the result that the reaction velocity (the esterification) is slightly influenced according to the pressure. For reasons of economy the process in accordance with the invention is preferably carried out at normal pressure. The addition of a strong acid as a catalyst greatly accelerates the esterification, which however also applies to the undesired esterification of the tocopherols.

Accordingly, it is unnecessary to catalyze the process in accordance with the invention, for example by adding an acid to the already weakly acidic (pH 5–6) deodorizer sludge. The addition of bases, for example sodium hydroxide, which are immediately neutralized by the fatty acids present, does not accelerate the ester formation, but instead lowers the yield of tocopherols a little, so that the addition of bases is also not advantageous, but is to be avoided if possible. With respect to the reaction temperature, it has been found that in general higher temperatures lead to shorter reaction times. For practical and economical reasons, the esterification, which is the essence of the process in accordance with the invention, is preferably effected in the temperature range from about 150° C. to about 250° C. in a time range of from about 1 to about 12 hours. In an especially preferred embodiment the esterification is carried out in the temperature range/time range of from about 180° C./2.5 hours to about 250° C./1.5 hours.

After the esterification of the deodorizer sludge by heating, the remaining fatty acids as well as other readily volatile components, which mainly have up to 20 carbon atoms per molecule, can be distilled off without too much loss of the desired tocopherols. The concentration of tocopherols in the residual liquid is thereby further increased. The fatty acid distillate obtained, which can be denoted as the "first distillation fraction", typically contains about 70 to 90 wt. % fatty acids and can be utilized as such; that is the fatty acids can be recovered if desired. This first distillation, which affords the first distillation fraction, is conveniently effected at about 0.1 mbar pressure and at heating bath (for example oil bath) temperatures in the range of from about 120° C. to about 150° C. A short-path evaporator can be used for example as the distillation apparatus. Of course, the distillation conditions can be varied depending on the content of the apparatus and the type and size of the apparatus.

After further distillation there is obtained a distillation fraction (the "second distillation fraction"), which, compared with the esterified deodorizer sludge, has a much higher content of tocopherols, typically about 15 to about 40 weight percent. The sterol esters formed in the esterification remain in the residue of the overall distillation, while any non-esterified sterols together with the majority of the tocopherols originally present are found in the second distillation fraction. These remaining sterols are not troublesome and can be separated with other impurities during the further processing of the second distillation fraction. The second distillation, which affords the second distillation fraction, is conveniently carried out at heating bath (for example oil bath) temperatures in the range of from about 200° C. to about 220° C. The convenient distillation conditions are in other respects analogous to the conditions given above in connection with the first distillation.

The remaining acidic components, mainly fatty acids, as well as squalene present in the second distillation fraction can be removed according to various methods in order to achieve a still greater enrichment of the tocopherols in the distillate. One such method comprises converting the acidic components into their corresponding esters, preferably methyl esters. The esterification, which is carried out in methanol, proceeds almost quantitatively and without essential loss of the tocopherols which are also present in the second distillation fraction. The esterification is conveniently catalyzed by traces of added acids, especially a mineral acid such as, for example, hydrochloric acid, and is carried out in a temperature range of from about 65° C. to about 100° C. A typical esterification with methanol proceeds at about 65° C. in the presence of hydrochloric acid as the catalyst and takes about 5 hours.

A further method for the removal of the acidic components and at the same time for the enrichment of the tocopherols in the distillate comprises treating the distillate with calcium hydroxide in the presence of water in an inert, water-miscible organic solvent, especially a lower alkanol such as, for example, isopropanol, and subsequently separating the thus-formed calcium salts. Because this salt formation is carried out in the presence of water, any glycerides still present are, moreover, saponified with the formation of calcium salts of fatty acids. The separation of the thus-obtained calcium salts is conveniently effected by removing the organic solvent used, for example distillation under reduced pressure, and precipitation from a suitable additional solvent, for example a lower alkyl formate or acetate, a readily volatile ketone or a readily volatile nitrile. This second method, which is, of course, foreseen for the enrichment of tocopherols in the deodorizer sludges described above but which can also be used for their enrichment in the second distillation fraction in question, is described in more detail and exemplified in European Patent Specification No. 316 729.

The concentrate resulting after the above described processing of the second distillation fraction (removal of the acidic components) can be subjected to an ion exchange procedure in order to selectively absorb the desired tocopherols, especially over a strongly basic resin. As phenols, the tocopherols exhibit a certain, although very weak, acidity. Accordingly, they can form salts, namely so-called "tocopherolates", with different kinds of strongly basic ion exchangers. For this purpose there can be used especially commercially available ion exchangers such as, for example, Amberlite®IRA 900, Amberlyst®A-26, Duolite®A-161 (all available from Rohm & Haas, Philadelphia, USA), Lewatit®500 MB (Bayer, Leverkusen, Germany), Dowex®1×2 and XUS®40240 (both available from Dow, Michigan, USA), of which Amberlite®IRA 900 is preferred. All six exemplified basic ion exchangers feature a tetraalkylammonium ion. The elution agent which is used is conveniently, inter alia, a lower alkanol, for example methanol, ethanol or isopropanol, or an aliphatic ketone, for example acetone. In this manner the majority of, if not all, further components are eluted and are consequently separated from the tocopherols. The latter can then be desorbed, for example with acetic acid/isopropanol mixtures, and potassium hydroxide or sodium hydroxide, especially their 4 percent solutions, can suitably be used for the regeneration of the resin. The tocopherol concentrate resulting after this ion exchange procedure has a very high purity, often above 93%. It has become evident that the identifiable accompanying substances, which are only present in traces, are homologues (precursors) such as, for example, δ-tocoenol, 65-tocoenol, 65-tododienol, 65-tocotrienol, α-tocoenol and the like, which also have vitamin E activity so that they must not be considered to be impurities. Accordingly, as a consequence of the ion exchange procedure, the achievable content of tocopherols is often more than 95%.

Finally, the concentrate obtained after the ion exchange procedure can be purified further by subjecting it to a flash distillation or bulb-tube distillation. Thereby, the residual solvent as well as traces of difficultly-volatile components (polymers, waxes etc.) are separated, whereby only a small loss of tocopherols, often not more than 2–3 weight percent, has to be reckoned with. In this manner a concentrate which has, for example, a tocopherol content of about 94% can be converted into a concentrate having a tocopherol content of about 97%. The distillation is conveniently carried out analogously to the first and second distillation described above, whereby however the convenient heating bath (for example oil bath) temperatures lie in the range of from about 240° C. to about 260° C. and a bulb-tube oven is used as the preferred distillation apparatus. The product of this distillation is the end product of the overall process for the separation of tocopherols from natural sources.

The residue obtained after the heating (esterification) of the deodorizer sludge and the subsequent distillation contains the majority of sterol esters which are formed in the esterification and from which the sterols themselves can be obtained. In addition to these difficultly volatile, wax-like sterol esters, the residue also contains triglycerides, other waxes as well as numerous high-molecular accompanying substances partly of unknown nature. The sterols are obtained by an acid-catalyzed trans-esterification of the fatty acid-sterol esters and of relatively small amounts of fatty acid-tocopherol esters with a lower alkanol, especially methanol or ethanol, to give the corresponding sterols, tocopherols and fatty acid alkyl esters. The trans-esterification is conveniently carried out in a steel autoclave. Concentrated sulphuric acid is preferably used as the acid catalyst and excess alkanol is preferably used as the solvent. Moreover, the trans-esterification is conveniently effected at temperatures between from about 70° C. and about 150° C. within a period of from about 1 to about 5 hours. An optimization of the yield of sterols can be achieved by the choice of suitable catalysts, solvents, reaction period and temperature. The main impurities, which are difficult to avoid, consist of dehydrated sterols, whereby, of course, a good yield of the desired sterols is usually achieved, not only with respect to the content of sterols in the original deodorizer sludge, but also in respect of the sterol content in the starting material (residue). For the complete separation of the sterols, the reaction solution is cooled, conveniently to about 0° C. By filtration of this solution, which contains crystals of sterols as a result of the cooling, the sterols can be separated from the mother liquor. The sterols and tocopherols remaining in the filtrate can be recycled, so that the yield of these in the overall procedure can be increased further in this manner.

The present invention is illustrated on the basis of the following Examples.

EXAMPLES 1

A sunflower oil distillate of the following composition was used as the starting material (deodorizer sludge).

|  | Wt. % |
| --- | --- |
| Tocopherols | 23.5 |
| Sterols | 12.5 |
| Fatty acids | 34 |
| Glycerides | 20 |
| Squalene | 2.4 |
| Remainder | 27.6 |

744 g of the above deodorizer sludge were heated at 170° C. under a water-jet vacuum for 9 hours in a rotary evaporator. After this esterification period there were obtained 721 g of "esterified" deodorizer sludge.

716 g of the esterified deodorizer sludge were subjected to a distillation at 0.1 mbar and at an oil temperature of 133° C. in a short-path evaporator (0.025 m$^2$) fitted with a double-jacketed dosing funnel and a needle valve. There were thus obtained 275.6 g of fatty acid distillate and 428.5 g of residue. After subsequent distillation of about 425 g of this residue at 0.1 mbar and 207° C. there were obtained 128.2 g of a concentrate as well as 296.1 g of residue. It was established that the concentrate has a 19.4% content of tocopherols, with the yield of tocopherols amounting to more than s 95% (based on the amount of tocopherols present in the starting material).

The whole of the above procedure was repeated with the difference that the esterification of the deodorizer sludge was carried out at 200° C. for 4 hours instead of at 170° C. for 9 hours. The results were similar.

EXAMPLE 2

A soya oil distillate of the following composition was used as the starting material (deodorizer sludge):

|  | Wt. % |
| --- | --- |
| Tocopherols | 10.2 |
| Sterols | 11.2 |
| Fatty acids and esters | 51.8 |
| Squalene | 1.9 |
| Remainder (glycerides and other high-molecular substances) | 24.9 |

Four esterifications were carried out with equal parts of the above deodorizer sludge under different conditions with respect to the esterification period. This consisted of a heating-up period (140°→200° C.) and a heating period at constant temperature (200° C.).

fractions [fatty acid fraction ("FaF") and tocopherol fraction ("TocF")] required for the evaluation are compiled in Table 2 below:

TABLE 2

| Experiment No. | (SPE 1) T(°C.) | (SPE 1) P(mbar) | SPE 2 T(°C.) | SPE 2 P(mbar) | Through put (g/h) | Fraction % FaF | Fraction % TocF | Remainder % | Fa in FaF (wt. %) | Toc in FaF (wt. %) | Fa in TocF (wt. %) | Toc in TocF (wt. %) | Loss of Toc (wt. %) |
|---|---|---|---|---|---|---|---|---|---|---|---|---|---|
| 1 | 145 | 0.25 | 165 | 0.05 | 479 | 30.3 | 37.5 | 32.2 | 40.2 | 0.9 | 29.8 | 17.1 | 44.8 |
| 2 | 145 | 0.1 | 200 | 0.05 | 392 | 39.8 | 34.9 | 25.5 | 70.6 | 1.6 | 18.0 | 33.6 | 5.5 |
| 3 | 150 | 0.25 | 210 | 0.02 | 887 | 39.6 | 31.9 | 28.5 | 62.6 | 1.5 | 34.5 | 29.8 | 5.9 |
| 4 | 145 | 0.25 | 200 | 0.016 | 908 | 32.2 | 33.7 | 35.0 | 74.2 | 0.9 | 50.5 | 25.6 | 4.0 |
| 5 | 160 | 0.25 | 210 | 0.016 | 747 | 41.9 | 24.5 | 33.0 | 59.9 | 1.7 | 28.3 | 34.6 | 8.0 |
| 6 | 155 | 0.25 | 210 | 0.02 | 751 | 37.8 | 29.3 | 33.3 | 75.0 | 1.1 | 36.9 | 29.9 | 5.0 |
| 7 | 156 | 0.25 | 205 | 0.01 | 750 | 38.6 | 28.6 | 32.8 | 73.4 | 1.2 | 34.5 | 29.7 | 6.0 |

Each of the esterifications was carried out in a 63 L stainless steel stirring vessel with jacket heating and an oil thermostat. After de-gassing for 1.5 hours at 60° C. /15 mmHg the respective deodorizer sludge was finally heated to 200° C. and held at this temperature. Subsequently, the composition of each esterification product was determined by gas chromatography. The results are given in Table 1 below:

TABLE 1

| Experiment | Educt | 1 | 2 | 3 | 4 |
|---|---|---|---|---|---|
| Heating up period (140→200° C.; h) | | 0.7 | 1.2 | 1.2 | 2.0 |
| Heating period (200° C.; h) | | 3.5 | 2.4 | 1.7 | 1.0 |
| Tocopherols (wt. %) | 10.2 | 8.7 | 8.9 | 9.4 | 9.4 |
| Sterols (wt. %) | 11.2 | 0.6 | 1.0 | 1.7 | 2.1 |
| Fatty acids and esters (wt. %) | 51.8 | 33.8 | 33.9 | 39.5 | 40.7 |
| Esterified tocopherols (wt. %) | | 14.0 | 12.1 | 7.9 | 7.4 |

The esterified deodorizer sludges from the four esterification experiments were combined prior to the subsequent distillation. The combined material had the following composition according to gas chromatography:

| | Wt. % |
|---|---|
| Tocopherols | 9.3 |
| Sterols | 1.6 |
| Fatty acids and esters | 39.4 |
| Squalene | 1.8 |
| Remainder | 46.6 |

The figures show that the tocopherol content decreased slightly (9.3 wt.% compared with 10.2 wt.%), while the content of sterols decreased considerably (1.6 wt. % compared with 11.2 wt.%). The sterol esters formed as a result of the heating were now present in the "remainder" material.

After the esterification a two-stage short-path distillation of portions of the combined esterified deodorizer sludge was carried out, namely in a distillation apparatus having two short-path evaporators (denoted hereinafter as "SPE 1" and, respectively, "SPE 2"). Not only the pressure ("P") but also the temperature ("T") in the two short-path evaporators were varied in order to determine the optimum operating conditions. The operating parameters essential for the optimization of the distillation conditions and the concentrations of fatty acids ("Fa") and tocopherols ("Toc") in the individual The figures show that, compared with the esterified deodorizer sludge (starting material for the distillation), the tocopherol fractions have a much higher content of tocopherols and in almost all instances a lower content of fatty acids. In turn, the fatty acid fractions, compared with the esterified deodorizer sludge, have a much higher content of fatty acids and a substantially lower content of tocopherols. The sterol esters were present in the "remainder" material. The loss of tocopherols was generally low.

EXAMPLE 3

A distillation fraction of the following composition was used as the starting material (a tocopherol fraction obtained according to the two-stage short-path distillation described in Example 2, that is a "second" distillation fraction) in the fatty acid esterification described below:

| | Wt. % |
|---|---|
| Tocopherols | 31 |
| Sterols | 5.1 |
| Fatty acids | 32 |
| Squalene | 4.9 |

99.6% of the tocopherol fraction were dissolved in 150 ml of methanol. 5 drops (about 100 mg) of 36% hydrochloric acid were added to the solution and the reaction mixture was heated at reflux temperature for 5 hours while stirring and gassing with argon. Thereafter, the mixture was cooled to room temperature and the solvent was evaporated off under reduced pressure. In this manner there were obtained 101.8 g of a concentrate which had a 30.3% content of tocopherols (about 100% yield) according to gas chromatography.

EXAMPLES 4

The concentrate prepared as described in Example 3 was used as the starting material in the ion exchange procedure described below. A glass column of 5 cm diameter filled with 150 g of Amberlite® IRA 900 (20–50 mesh) was used in this procedure. The concentrate had the following composition at the beginning;

| | Wt. % |
|---|---|
| Tocopherols | 30.3 |
| Sterols | 5.8 |

-continued

| | Wt. % |
|---|---|
| Squalene | 4.6 |

The resin (Amberlite® IRA 900, 20–50 mesh; acetate form) was washed with 200 ml of deionized water and subsequently activated with 1 L of 4% aqueous potassium hydroxide. The excess potassium hydroxide solution was removed with 300 ml of deionized water and, in turn, the water was displaced by 600 ml of methanol. 101.3 g of the above concentrate were dissolved in 250 ml of isopropanol and the resulting solution was added to the resin. Then, the column was eluted with 400 ml of isopropanol in order to separate the accompanying substances. Subsequently, 200 ml of a methanol/acetic acid (4:1) mixture were added to the resin and the thus-moistened resin was left to stand for about 3 hours, with the tap remaining closed. Thereafter, the tocopherols were eluted completely with 600 ml of methanol and the resulting acidic, tocopherol-containing methanol solution (about 800 ml) was then concentrated under reduced pressure. The thus-obtained crude product (about 94% tocopherol content according to gas chromatography) was distilled in a bulb-tube oven (GKR 50) at 250° C. and 0.1 mbar. In this manner there were obtained 29.5 g of a light yellowish oil with an about 96% content of tocopherols (according to gas chromatography; 92% yield).

EXAMPLE 5

Analogously to the procedure described in Example 4, from 50.0 g of a concentrate which had a 63.1% content of tocopherols, a 9.5% content of sterols and triterpenes and an 8.6% content of squalene there were obtained 30.6 g of a light yellowish oil. This oil contained about 96.5 weight percent of tocopherols (93.6% yield).

EXAMPLE 6

The same concentrate which was described in Example 5 was used as the starting material in the ion exchange procedure described below. The glass column of 5 cm diameter was filled with 180 g of Amberlite® IRA 900 (20–50 mesh). This resin was washed with 200 ml of deionized water and subsequently reactivated with 1 L of 4% aqueous potassium hydroxide solution. The excess potassium hydroxide solution was removed with 300 ml of deionized water and this in turn was forced out at an inert gas over-pressure of 0.1 bar. The remaining water was displaced with 300 ml of isopropanol. 40.3 g of the above concentrate were dissolved in 230 ml of isopropanol and the resulting solution was added to the resin. Then, the column was eluted with 400 ml of isopropanol in order to separate the accompanying substances. Subsequently, 200 ml of an isopropanol/acetic acid (4:1) mixture were added to the resin and the thus-moistened resin was left to stand for about 3 hours, with the tap remaining closed. Thereafter, the tocopherols were eluted completely with a further 400 ml of the isopropanol/acetic acid mixture, the remaining mixture was pressurized with an inert gas over-pressure of 0.1 bar and the resulting acidic, tocopherol-containing methanol solution (about 600 ml) was then concentrated under reduced pressure. The thus-obtained crude product was distilled in a bulb-tube oven (GKR 50) at 250° C. and 0.1 mbar. In this manner there were obtained 24.3 g of a light yellowish oil with an about 96.5% content of tocopherols (according to gas chromatography; 92.3% yield).

EXAMPLE 7

A residue which resulted from the esterification of a soya oil deodorizer sludge (as described, for example, in Example 1 or 2) was used as the starting material in the sterol production procedure described in this Example. 15 g of such a residue containing 4.9 g of sterols as sterol esters, 150 ml of methanol as well as 1.5 g of concentrated sulphuric acid were placed in a 250 ml steel autoclave provided with a thermometer and magnetic stirrer. This was then immersed in an oil bath pre-heated to 95° C. and the contents of the autoclave were stirred at this temperature for 3 hours. After cooling the solution to room temperature, the autoclave was emptied and the solution was left at 0° C. for 1 hour in a round flask for the complete crystallization of the sterols formed in the reaction. Subsequently, the sterols were filtered off, washed with a small amount of cold methanol and dried for 1 hour at 60° C. under a high vacuum. 4.9 g of a beige powder were obtained in this manner. According to gas chromatography the yield of sterols amounted to 90% based on the original deodorizer sludge or almost 100% based on the starting material (the residue of the deodorizer sludge esterification). The procedure described above produced different results with respect to the yield of sterols and the quality of the end product (percentage content of sterols in the product) with varying reaction time and internal temperature (of the reaction mixture). The results of 5 experiments using the same residue as above (content of sterols 32.5 wt.%) are given in Table 3 below:

TABLE 3

| Experiment | Reaction time (hours) | Internal temp. (°C.) | Sterol yield | End product quality |
|---|---|---|---|---|
| 1 | 5 | 105 | 57% | 63% sterols (+24% dehydrated sterols) |
| 2 | 2 | 105 | 75% | 83% sterols |
| 3 | 1 | 100 | 80% | 88% sterols |
| 4 | 2 | 85 | 76% | 70% sterols |
| 5 | 3 | 85 | 90% | 90% sterols |

I claim:

1. A process for separating tocopherols and sterols from deodorizer sludges comprising sterols, fatty acids, and tocopherols, said process consisting essentially of the steps of:

(a) esterifying the sterols in the deodorizer sludge with fatty acids which are also present in the deodorizer sludge to form a mixture comprising sterol fatty acid esters, fatty acids, and tocopherols;

(b) distilling said mixture to obtain a first distillation fraction containing fatty acid residues, a second distillation fraction containing tocopherols, and a sterol fatty acid ester residue;

(c) isolating the tocopherols from the second distillation fraction; and (d) isolating the sterols from the sterol fatty acid ester residue.

2. The process according to claim 1, wherein a distillate from the deodorization of a vegetable oil or fat is used as the deodorizer sludge.

3. The process according to claim 2, wherein said vegetable oil is selected from the group consisting of sunflower oil, soya oil, rape oil, cottonseed oil, palm oil, groundnut oil, and wheatgerm oil.

4. The process according to claim 1, wherein the deodorizer sludge is de-gassed prior to the esterification.

5. The process according to claim 1, wherein the esterification is carried out at normal pressure.

6. The process according to claim 1, wherein the deodorizer sludge is esterified by heating said deodorizer sludge in a temperature range from about 150° C. to about 250° C. in a time range of from about 1 to about 12 hours.

7. The process according to claim 6, wherein the heating is carried out in a temperature range from about 150° C. to about 220° C.

8. The process according to claim 6, wherein the heating is carried out in a temperature range and time range of from about 180° C. for about 2.5 hours to about 250° C. for about 1.5 hours.

9. A process for separating tocopherols and sterols from deodorizer sludges comprising the steps of:

(a) esterifying the sterols in the deodorizer sludge with fatty acids which are also present in the deodorizer sludge containing sterol esters by heating the deodorizer sludge in a temperature range from about 150° C. to about 250° C. in a time range of from about 1 to about 12 hours to form an esterified sterol deodorizer sludge containing sterol esters;

(b) distilling said esterified sterol deodorizer sludge to form a fatty acid distillate and a residue;

(c) distilling said residue to form a distillate containing tocopherols and a residue containing esterified sterols;

(d) isolating the tocopherols from the distillate containing tocopherols; and (e) isolating the sterols from the residue containing esterified sterols.

10. The process according to claim 9, wherein the heating is carried out in a temperature range from about 150° C. to about 220° C.

11. The process according to claim 9, wherein the heating is carried out in a temperature range and time range of from about 180° C. for about 2.5 hours to about 250° C. for about 1.5 hours.

* * * * *